United States Patent
Hickman et al.

(10) Patent No.: US 10,168,690 B2
(45) Date of Patent: *Jan. 1, 2019

(54) METHODS AND SYSTEMS FOR MULTIROBOTIC MANAGEMENT

(71) Applicant: X Development LLC, Mountain View, CA (US)

(72) Inventors: Ryan Hickman, Mountain View, CA (US); Chaitanya Gharpure, Sunnyvale, CA (US)

(73) Assignee: X Development LLC, Mountain View, CA (US)

(*) Notice: Subject to any disclaimer, the term of this patent is extended or adjusted under 35 U.S.C. 154(b) by 271 days.

This patent is subject to a terminal disclaimer.

(21) Appl. No.: 15/337,095

(22) Filed: Oct. 28, 2016

(65) Prior Publication Data

US 2017/0083005 A1 Mar. 23, 2017

Related U.S. Application Data

(63) Continuation of application No. 14/679,457, filed on Apr. 6, 2015, now Pat. No. 9,513,624, which is a (Continued)

(51) Int. Cl.
*G05B 19/418* (2006.01)
*A23B 5/06* (2006.01)
(Continued)

(52) U.S. Cl.
CPC .......... *G05B 19/418* (2013.01); *A01N 25/10* (2013.01); *A23B 5/06* (2013.01); *B25J 3/00* (2013.01); *Y02P 90/02* (2015.11)

(58) Field of Classification Search
CPC ........ A23B 5/06; A01N 25/10; G05B 19/418; H05K 7/1462; H05K 7/1464;
(Continued)

(56) References Cited

U.S. PATENT DOCUMENTS 5,819,008 A  10/1998  Asama et al.
6,408,226 B1 *  6/2002  Byrne .................. G05D 1/0246
                                           318/568.11
(Continued)

FOREIGN PATENT DOCUMENTS

JP        405065766 A    3/1993
WO    WO 2009-040777 A2  4/2009

OTHER PUBLICATIONS

Mokarizadeh, S., et al., "Applying Semantic Web Service Composition for Action Planning in Multi-Robot Systems," 2009 Fourth International Conference on Internet and Web Applications and Services, May 24, 2009.
(Continued)

*Primary Examiner* — Stephen Holwerda
(74) *Attorney, Agent, or Firm* — McDonnell Boehnen Hulbert & Berghoff LLP (57) ABSTRACT

Multirobotic management can involve communications between a command or leader robot and one or more client or follower robots through a cloud computing system. In an example implementation, a leader robot can receive first sensory data captured by a first follower robot and second sensory data captured by a second follower robot, determine a command function based on at least one of the first sensory data and the second sensory data, and communicate with at least one of the first follower robot and the second follower robot based on the command function.

17 Claims, 6 Drawing Sheets

Related U.S. Application Data continuation of application No. 13/446,030, filed on May 7, 2012, now Pat. No. 9,026,248.

(60) Provisional application No. 61/593,078, filed on Jan. 31, 2012, provisional application No. 61/483,295, filed on May 6, 2011.

(51) Int. Cl.
*A01N 25/10* (2006.01)
*B25J 3/00* (2006.01)

(58) Field of Classification Search
CPC .. H05K 7/1465; G05D 1/0274; G05D 1/0225; G05D 1/0276; G05D 1/028; G05D 1/0285
USPC ... 318/568.1, 568.11, 568.12, 568.16, 568.2; 700/245, 246, 247, 248, 250, 253, 258, 700/259
See application file for complete search history.

(56) References Cited

U.S. PATENT DOCUMENTS

| | | | |
|---|---|---|---|
| 6,491,566 B2 | 12/2002 | Peters et al. | |
| 6,687,571 B1 | 2/2004 | Byrne et al. | |
| 2002/0137427 A1* | 9/2002 | Peters | A63H 30/04 446/454 |
| 2002/0138179 A1* | 9/2002 | Payton | G05D 1/0242 701/1 |
| 2003/0105534 A1 | 6/2003 | Hara et al. | |
| 2003/0141837 A1 | 7/2003 | Young et al. | |
| 2003/0212472 A1 | 11/2003 | McKee | |
| 2004/0139110 A1 | 7/2004 | LaMarca et al. | |
| 2005/0021186 A1 | 1/2005 | Murray, IV et al. | |
| 2006/0047377 A1* | 3/2006 | Ferguson | E02F 9/205 701/2 |
| 2006/0095158 A1* | 5/2006 | Lee | H04M 1/72533 700/245 |
| 2006/0114324 A1 | 6/2006 | Farmer et al. | |
| 2006/0146776 A1* | 7/2006 | Kim | B25J 9/1602 370/338 |
| 2006/0184292 A1 | 8/2006 | Appleby et al. | |
| 2006/0253224 A1 | 11/2006 | Tani et al. | |
| 2009/0099768 A1* | 4/2009 | Bauer | G01C 21/005 701/467 |
| 2010/0145514 A1 | 6/2010 | Kim et al. | |
| 2011/0143811 A1 | 6/2011 | Rodriguez | |

OTHER PUBLICATIONS

Walker, J., et al., "A Performance Sensitive Hormone-Inspired System for Task Distribution Amongst Evolving Robots," 2008 IEEE/RSJ International Conference on Intelligent Robots and Systems, Sep. 22, 2008.

Correll, N., "Parameter Estimation and Optimal Control of Swarm-Robotic Systems: A Case Study in Distributed Task Allocation," 2008 IEEE International Conference on Robotics and Automation, May 19, 2003.

* cited by examiner

METHODS AND SYSTEMS FOR MULTIROBOTIC MANAGEMENT

CROSS-REFERENCE TO RELATED APPLICATIONS

The present application is a continuation of U.S. patent application Ser. No. 14/679,457, filed on Apr. 6, 2015, which is a continuation of U.S. patent application Ser. No. 13/466,030, filed on May 7, 2012, which claims priority to U.S. Patent Application No. 61/483,295, filed on May 6, 2011, and to U.S. Patent Application No. 61/593,078, filed on Jan. 31, 2012, all of which are herein incorporated by reference.

BACKGROUND

Cloud computing refers to provision of computational resources via a computer network. In a traditional model of computing, both data and software are fully contained on a user's computer. In cloud computing, however, the user's computer may contain relatively little software or data (perhaps a minimal operating system and web browser, for example), and may serve as a display terminal for processes occurring on a network of computers. A common shorthand provided for a cloud computing service or system (or even an aggregation of existing cloud services) is "the cloud."

Cloud computing has been referred to as "client-server computing", however, there may be distinctions between general cloud computing and client-server computing. For example, client-server computing may include a distributed application structure that partitions tasks or workloads between providers of a resource or service (e.g., servers), and service requesters (e.g., clients). Client-server computing generally involves a one-to-one relationship between the server and the client, whereas cloud computing includes generic services that can be accessed by generic clients (e.g., a one-to-one relationship or connection may not be required). Thus, cloud computing generally includes client-server computing, and additional services and functionality.

BRIEF SUMMARY

In one aspect of this disclosure, a first example method is provided. The first example method involves receiving, by a leader robot, first sensory data captured by a first follower robot and second sensory data captured by a second follower robot. The first follower robot has a first sensing capability and the second follower robot has a second sensing capability that is different than the first sensing capability. The leader robot is configured to communicate with the first follower robot and the second follower robot and to direct action of one or more of the first follower robot and the second follower robot. The first example method further involves determining a command function based on at least one of the first sensory data and the second sensory data. The first example method still further involves communicating with at least one of the first follower robot and the second follower robot based on the command function.

In another aspect of this disclosure, a second example method is provided. The second example method involves receiving, by a command robot, data captured by one or more client robots in a plurality of client robots. The command robot is configured to communicate with each of the plurality of client robots and to direct action of one or more of the plurality of client robots. Each client robot in the plurality of client robots has a respective data capture capability and is configured to communicate with the command robot through a cloud computing system. The second example method further involves determining a command function based on the data captured by the one or more client robots. The second example method still further involves communicating with at least one client robot in the plurality of client robots based on the command function.

In still another aspect of this disclosure, an example system is provided. The example system includes a command robot and a plurality of client robots. The command robot is configured to communicate with each of the plurality of client robots and to direct action of one or more of the plurality of client robots. Each client robot includes at least one sensor, a client-robot processor, a client-robot memory, and client-robot program instructions stored in the client-robot memory and executable by the client-robot processor to perform client-robot operations, involving capturing data from the at least one sensor, capturing data from an electronic device, and communicating with the command robot through a cloud computing system. The command robot includes a command-robot processor, a command-robot memory, and command-robot program instructions stored in the command-robot memory and executable by the command-robot processor to perform command-robot operations, involving communicating with each client robot through the cloud computing system, analyzing data captured by each client robot, determining a command function based on the analyzed data, and communicating with one or more of the client robots based on the command function.

In yet aspect of this disclosure, an example article of manufacture is provided. The example article of manufacture includes a computer-readable storage medium, having stored thereon program instructions that, upon execution by a computing device, cause the computing device to perform operations. The operations include: (a) receiving first sensory data captured by a first robot and second sensory data captured by a second robot, in which the first robot has a first sensing capability and the second robot has a second sensing capability that is different than the first sensing capability; (b) determining a command function based on at least one of the first sensory data and the second sensory data; and (c) communicating with at least one of the first robot and the second robot based on the command function.

The foregoing summary is illustrative only and is not intended to be in any way limiting. In addition to the illustrative aspects, embodiments, and features described above, further aspects, embodiments, and features will become apparent by reference to the Figures and the following Detailed Description.

DETAILED DESCRIPTION

In the following detailed description, reference is made to the accompanying Figures, which form a part hereof. In the Figures, similar symbols typically identify similar components, unless context dictates otherwise. The illustrative embodiments described in the detailed description, Figures, and claims are not meant to be limiting. Other embodiments may be utilized, and other changes may be made, without departing from the scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

This disclosure generally relates to a robotic method and system where a command capability, such as a command robot, has data input from a plurality of other robots, with the command robot being able to coordinate the activities of the other robots through a cloud computational system or resource, and in particular, to allocate tasks between the other robots in a manner best suited for the state and capability of each other robot.

In particular, but without limitation, the disclosure provides for a first robot that may have a function which enables the robot to assess the vicinity of the robot, or environment, for environmental data capture. A second robot may have similar function, but may be different in functionality and/or have different data capture from the first robot. A command robot, or centralized command, has a functionality which communicates with the first and second robots, as client robots, through a cloud computational system, and then draw conclusions, results or determinations for some function for the first and/or second robot to execute as a result of the analysis performed, such as through a coordinated allocation of tasks based upon the state or capability of a respective robot.

This disclosure includes, inter alia, methods and systems for robot and user interaction over the cloud. Within examples, cloud-based computing generally refers to networked computer architectures in which application execution and storage may be divided, to some extent, between client and server devices. A robot may be any device that has a computing ability and interacts with its surroundings with an actuation capability (e.g., electromechanical capabilities). A client device may be configured as a robot including various sensors and devices in the forms of modules, and different modules may be added to the robot or removed from the robot depending on requirements. In some examples, a robot may be configured to receive a second device, such as mobile phone, that may be configured to function as an accessory or a "brain" of the robot.

In examples described herein, a robot may interact with the cloud to perform any number of actions, such as to share information with other cloud computing devices. Within examples, a robot may interact with a user in a manner that is based upon many types of received information. A robot may access a user device to determine or identify information about a user or related to the user, and the robot may be configured to tailor a method of interaction with the user based on the identified information. A robot may further receive data associated with the user to identify the user, such as using speech or face recognition. The robot may provide a personalized interaction or response to the user based on the determined information of the user.

In some instances, the "default user-profile" may simply be referred to as a "user-profile." Further, the user-profile may be linked to other profiles that the user has created, as on social networking sites, such that the robot can access up-to-date and accurate information regarding the user. The user-profile may include information corresponding to the user's personality, history, lifestyle, preferences, and/or predispositions. The robot may use such information when interacting with the user.

This disclosure provides methods and apparatus for a robotic method and system that has a function or capability for directing, as by coordinating, a plurality of robots some or all of which may have a data capture capability for assessing the environment or vicinity of the robot and/or a user or subject. The term "environment" will be used in this disclosure as a generic reference to whatever may be assessed in the way of conditions in the local vicinity of the robot, or a remote vicinity, which may be where a user or a robot is located or may be located at some future time, or where there is some interest presented to the robot or user. The plurality of robots are sometimes referred to herein as "client" or "follower" robots, as these client robots will be subject to a command robot or central command control.

In one aspect, a robot includes a computer processor, memory and operating system, with at least one sensory device capturing data relating to environmental conditions in the vicinity of the robot. The robot can also include a further data capture capability for electronic data capture.

That environmental input may be processed to obtain and retrieve information regarding a state of the environment drawn from an informational source containing environmental information, which may be residing in the robotic apparatus memory, may be otherwise accessible locally, or may be remote, as in a cloud computing system. The environmental input may be obtained variously from among a plurality of different robots, thereby constituting multiple different inputs. So too, the one or more robots may be capturing or acquiring electronic data from its environment or otherwise in the course of what that robot is currently doing.

The one or more environmental inputs may then be variously accessed by a command or leader robot, particularly through a cloud computing system, which analyzes and processes the input(s) for directing, as by coordinating, the further activity of one or more of the robots.

That response by the command robot to obtaining the input data from another robot(s), may be processing of the sensory input to extract environment information regarding a state of the environment drawn from the robot sensory input and/or an informational source containing environment information. That retrieved environment information is then used in performing an output function for the robot(s), which may be an interaction with a user, or with the environment itself.

An aspect of the disclosure provides a method for multirobot interaction and coordination, having a first robot with a first sensing capability and a second robot with a second sensing capability. Each robot has a communication link with a cloud computing system.

A robot control command program communicates with each robot through at least the cloud computing system (centralized command), but could additionally or in lieu thereof operate through some other communication medium; this could be local data transfer between robots or a database.

The command program analyzes data capture obtained by each robot through that robot's respective sensing capability. The command program then performs a command function for the first and/or second robots using the data obtained from each robot.

In an aspect, the method may include executing the command function to determine and then distribute data capture from the first robot to the second robot. That may be to coordinate an ongoing activity of each robot.

In an aspect, the disclosure contemplates multiple interchanges between command and client robots. For example, the data capture from the first robot is analyzed through the command program, then provided as a first input to the second robot. This could be, for instance, the first robot may be capable of determining the temperature in a part of a building, and that information is then processed by the command robot and provided as first input to a second robot in another area of the building, perhaps in a location where temperature adjustment is effected for the building. This embodiment of the method would then further include obtaining initial feedback from said second robot based upon said first input. Using the foregoing example, the second robot may then effect a change in the temperature of the building. The command robot then analyzes the initial data feedback from the second robot, obtaining further data capture from the second robot. Again using the foregoing example, that data capture may be the change in temperature manipulated by the second robot. The command robot then analyzes the further data capture, and provides a further command function using the further data capture analysis. That further command function may be using the further data capture from the second robot to provide a second data input to the first robot (e.g., "building heat/cool has been modified"), and obtaining a secondary feedback from the first robot based upon the second data input (e.g., detecting a changed temperature in the vicinity of the first robot), analyzing the secondary data feedback from the first robot, and providing a still further command function using the secondary feedback analysis (e.g., determining that the temperature of the room sensed in the area of the first robot has not been adequately modified, and therefore commanding the second robot to effect a further temperature manipulation).

In a further aspect of the disclosure, a method and system for multirobot interaction and coordination uses a plurality of client robots including at least a first and second client robot, each client robot having a data capture capability. Each client robot can have a respective communication link with a cloud computing system.

A command robot has a control command program which communicates with each client robot through at least the referred cloud computing system. The command program analyzes data capture obtained by each client robot through a respective data capture capability of that client robot. The command robot then performs a command function for one or more of the client robots using the data capture obtained from one or more of the client robots. That command function may be to coordinate an ongoing activity of each client robot. It could be a method and system where at least one or more of the client robots has a functional capability different from another of the client robots, and the command function is to allocate a task or tasks to a client robot having a preferred functionality for performing the task or tasks.

In some embodiments, each client robot includes a processor, at least one sensor detecting data in the vicinity of the client robot, and memory including instructions stored thereon executable by the processor to perform functions of: obtaining data capture from (1) an electronic device, and (2) environment sensory input data regarding sensed environment condition by the client robot. Each client robot can have a respective communication link with a cloud computing system.

The command robot has a command processor and command memory including a control command program which has instructions executable by the command processor to perform functions of communicating with each client robot through at least the cloud computing system, analyzing data capture obtained by each client robot, and performing a command function for one or more of the client robots using the data capture obtained from one or more of the client robots. This method and system may be repeated as between data gathering by the client robots, analysis by the command robot with a command function based thereon, feedback from a client robot in view of the command function, and further data gathering, analysis, command function, feedback and so on. The command function may be to determine and then distribute data capture from a first client robot to a second client robot in this manner. Further, the command function may be to coordinate an ongoing activity of each of the first and second client robots. It will be understood that the number of client robots is not limited to just two, but can be as many as desired. The command robot may also be a distributed system, comprising modules functioning as a command apparatus, device or system.

Visual imaging can determine aspects of the environment of a client robot. The robot could also sense other electromagnetic radiation (such as infrared), acoustic (such as ultrasound), and tactile observations, to name but a few. It is an aspect of the disclosure that the various sensory inputs would be processed either locally, or more through a cloud-based computational system.

Any of the methods and systems described herein may be provided in a form of instructions stored on a non-transitory, computer readable medium, that when executed by a computing device, cause the computing device to perform any of the methods described herein. Further examples may also include articles of manufacture including tangible computer-readable media that have computer-readable instructions encoded thereon, and the instructions may comprise instructions to perform any of the methods described herein.

The computer readable medium may include non-transitory computer readable medium, for example, such as computer-readable media that stores data for short periods of time like register memory, processor cache and Random Access Memory (RAM). The computer readable medium may also include non-transitory media, such as secondary or persistent long term storage, like read only memory (ROM), optical or magnetic disks, compact-disc read only memory (CD-ROM), for example. The computer readable media may also be any other volatile or non-volatile storage systems. The computer readable medium may be considered a computer readable storage medium, for example, or a tangible storage medium.

In addition, circuitry may be provided that is wired to perform logical functions in any processes or methods described herein.

In still further examples, any type of devices may be used or configured to perform logical functions in any processes or methods described herein. Robotic apparatus and robot are therefore used in the broadest sense.

In yet further examples, any type of devices may be used or configured as means for performing functions of any of the methods described herein (or any portions of the methods described herein).

1. Cloud Computing Architecture

Figure 1:
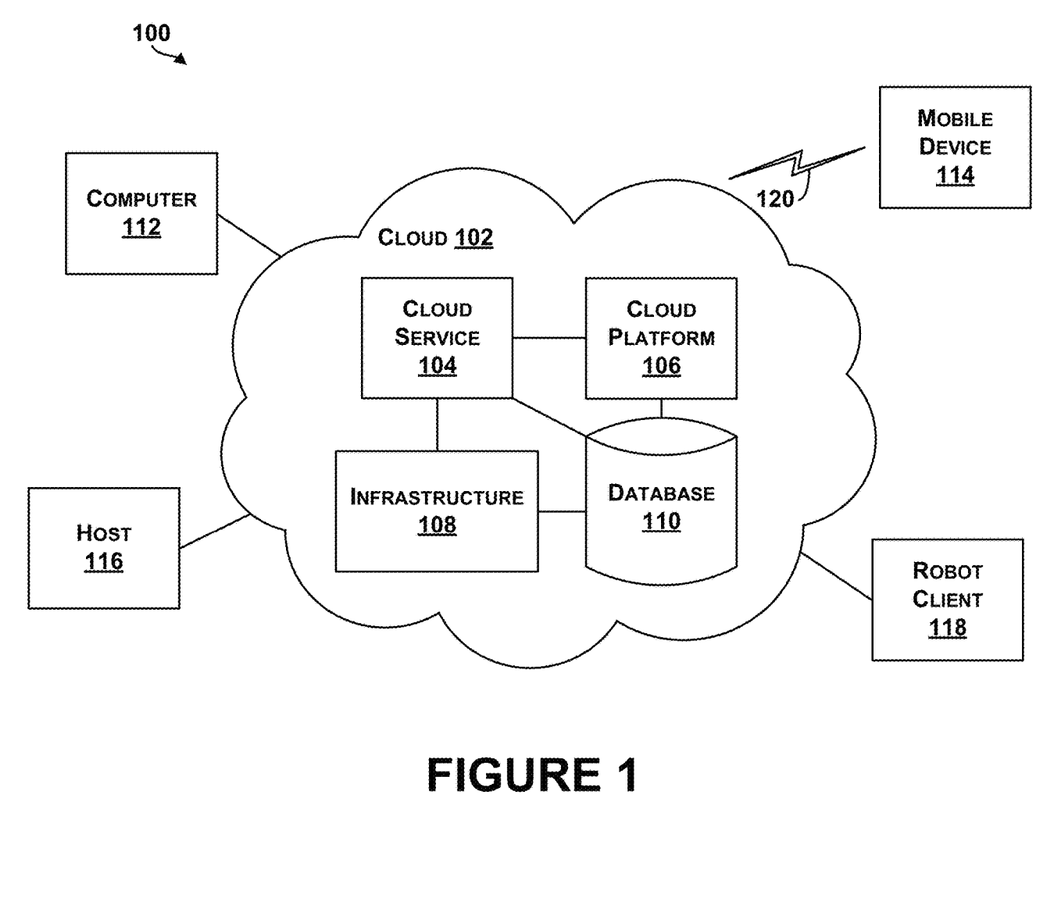
FIG. 1 is an example system for cloud-based computing.

Referring now to the Figures, FIG. 1 is an example system 100 for cloud-based computing. Cloud-based computing generally refers to networked computer architectures in which application execution and storage may be divided, to some extent, between client and server devices. A "cloud" may refer to a service or group of services accessible over a network (e.g., Internet) by client and server devices, for example.

In one example, any computer connected to the cloud may be connected to the same pool of computing power, applications, and files. Thus, cloud computing enables a shared pool of configurable computing resources (e.g., networks, servers, storage, applications, and services) that can be provisioned and released with minimal management effort or service provider interaction. Users can store and access personal files such as music, pictures, videos, and bookmarks or play games or use productivity applications on a remote server rather than physically carrying around a storage medium.

As an example, in contrast to a predominately client-based or server-based application, a cloud-based application may store copies of data and/or executable program logic at remote server devices, while allowing client devices to download at least some of this data and program logic as needed for execution at the client devices. In some examples, downloaded data and program logic can be tailored to capabilities of specific client devices (e.g., a personal computer, tablet, or mobile phone, or robot) accessing the cloud based application. In addition, dividing application execution and storage between the client and server devices allows more processing to be performed by the server devices taking advantage of server devices processing power and capability, for example.

Cloud-based computing can also refer to distributed computing architectures in which data and program logic for a cloud-based application are shared between one or more client devices and/or server devices on a near real-time basis. Parts of this data and program logic may be dynamically delivered, as needed or otherwise, to various clients accessing the cloud-based application. Details of the architecture may be transparent to users of client devices. Thus, a PC user or robot client device accessing a cloud-based application may not be aware that the PC or robot downloads program logic and/or data from the server devices, or that the PC or robot offloads processing or storage functions to the server devices, for example.

In FIG. 1, a cloud 102 includes a cloud service 104, a cloud platform 106, a cloud infrastructure 108, and a database 110. The cloud 102 may include more of fewer components, and each of the cloud service 104, the cloud platform 106, the cloud infrastructure 108, and the database 110 may comprise multiple elements as well. Thus, one or more of the described functions of the system 100 may be divided up into additional functional or physical components, or combined into fewer functional or physical components. In some further examples, additional functional and/or physical components may be added to the examples illustrated by FIG. 1. Delivery of cloud computing may involve multiple cloud components communicating with each other over application programming interfaces, such as web services and three-tier architectures, for example.

The cloud 102 may represent a networked computer architecture, and in one example, the cloud service 104 represents a queue for handling requests from client devices. The cloud platform 106 may include a frontend of the cloud and may be coupled to the cloud service 104 to perform functions to interact with client devices. The cloud platform 106 may include applications used to access the cloud 102 via a user interface, such as a web browser. The cloud infrastructure 108 may include service application of billing components of the cloud 102, and thus, may interact with the cloud service 104. The database 110 may represent storage capabilities by the cloud 102, and thus, may be accessed by any of the cloud service 104, the cloud platform 106, and/or the infrastructure 108.

The exemplary system 100 includes a number of client devices coupled to or configured to be capable of communicating with components of the cloud 102. For example, a computer 112, a mobile device 114, a host 116, and a robot client 118 are shown coupled to the cloud 102. Of course, more or fewer client devices may be coupled to the cloud 102. In addition, different types of client devices may be coupled to the cloud 102. For example, any of the client devices may generally comprise a display system, memory, and a processor.

The computer 112 may be any type of computing device (e.g., PC, laptop computer), and the mobile device 114 may be any type of mobile computing device (e.g., laptop, mobile telephone, cellular telephone).

The host 116 may be any type of computing device or transmitter including a laptop computer, a mobile telephone, that is configured to transmit data to the cloud 102.

The robot client 118 may comprise any computing device that has connection abilities to the cloud 102 and that has an actuation capability (e.g., electromechanical capabilities). A robot may further be a combination of computing devices. In some examples, the robot 118 may collect data and upload the data to the cloud 102. The cloud 102 may be configured to perform calculations or analysis on the data and return processed data to the robot client 118. In some examples, as shown in FIG. 1, the cloud 102 may include a computer that is not co-located with the robot client 118. In other examples, the robot client 118 may send data to a second client (e.g., computer 112) for processing.

Any of the client devices may include additional components. For example, the robot client 118 may include one or more sensors, such as a gyroscope or an accelerometer to measure movement of the robot client 118. Other sensors may further include any of Global Positioning System (GPS) receivers, infrared sensors, optical sensors (still image or motion picture), biosensors, Radio Frequency identification (RFID) systems, RADAR wireless sensors, haptic arrays and other touch sensors, and/or compasses, among others, for example.

In addition, any of the client devices may include an integrated user-interface (UI) that allows a user to interact with the device. For example, the robot client 118 may include various buttons and/or a touchscreen interface that allow a user to provide input. As another example, the robot client device 118 may include a microphone configured to receive voice commands from a user. Furthermore, the robot client 118 may include one or more interfaces that allow various types of user-interface devices to be connected to the robot client 118.

In FIG. 1, communication links between client devices and the cloud 102 may include wired connections, such as a serial or parallel bus. Communication links may also be wireless links, such as link 120, which may include Bluetooth, IEEE 802.11 (IEEE 802.11 may refer to IEEE 802.11-2007, IEEE 802.11n-2009, or any other IEEE 802.11 revision), or other wireless based communication links.

In other examples, the system 100 may include access points through which the client devices may communicate with the cloud 102. Access points may take various forms, for example, an access point may take the form of a wireless access point (WAP) or wireless router. As another example, if a client device connects using a cellular air-interface protocol, such as a CDMA or GSM protocol, an access point may be a base station in a cellular network that provides Internet connectivity via the cellular network.

As such, the client devices may include a wired or wireless network interface through which the client devices can connect to the cloud 102 (or access points). As an example, the client devices may be configured to use one or more protocols such as 802.11, 802.16 (WiMAX), LTE, GSM, GPRS, CDMA, EV-DO, and/or HSPDA, among others.

Furthermore, the client devices may be configured to use multiple wired and/or wireless protocols, such as "3G" or "4G" data connectivity using a cellular communication protocol (e.g., CDMA, GSM, or WiMAX, as well as for "WiFi" connectivity using 802.11). Other examples are also possible.

2. Example Robot Architecture

Figure 2A:
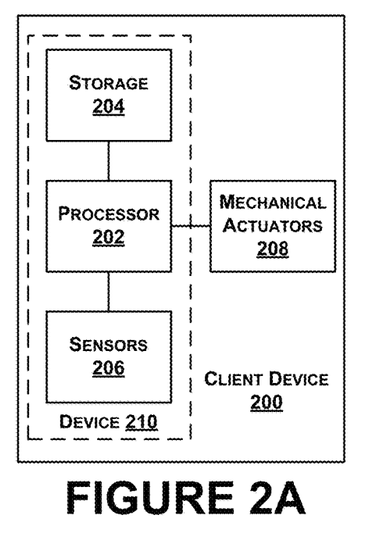
FIG. 2A illustrates an example client device.

FIG. 2A illustrates an example client device 200. In one example, the client device 200 is configured as a robot. In some examples, a robot may contain computer hardware, such as a processor 202, memory or storage 204, and sensors 206. For example, a robot controller (e.g., processor 202, computing system, sensors 206) may all be custom-designed for a specific robot. The robot may have a link by which the link can access cloud servers (as shown in FIG. 1). A wired link may include, for example, a parallel bus or a serial bus such as a Universal Serial Bus (USB). A wireless link may include, for example, Bluetooth, IEEE 802.11, Cellular (such as GSM, CDMA, UMTS, EV-DO, WiMAX, or LTE), or Zigbee, among other possibilities.

In one example, the storage 204 may be used for compiling data from various sensors 206 of the robot and storing program instructions. The processor 202 may be coupled to the storage 204 and may be configured to control the robot based on the program instructions. The processor 202 may also be able to interpret data from the various sensors 206 on the robot, as discussed above.

The client device 200 may also have components or devices that allow the client device 200 to interact with its environment. For example, the client device 200 may have mechanical actuators 208, such as motors, wheels 222, movable arms 220, that enable the client device 200 to move or interact with the environment.

In some examples, various sensors and devices on the client device 200 may be modules. Different modules may be added or removed from a client device 200 depending on requirements. For example, in a low power situation, a robot may have fewer modules to reduce power usages. However, additional sensors may be added as needed. To increase an amount of data a robot may be able to collect, additional sensors may be added, for example.

In some examples, the client device 200 may be configured to receive a device, such as device 210, that includes the processor 202, the storage 204, and the sensors 206. For example, the client device 200 may be a robot that has a number of mechanical actuators (e.g., a movable base), and the robot may be configured to receive a mobile telephone to function as the "brains" or control components of the robot. The device 210 may be considered a module of the robot. The device 210 may be physically attached to the robot. For example, a mobile phone may sit on a robot's "chest" and form an interactive display. The device 210 may provide a robot with sensors, a wireless link, and processing capabilities, for example. The device 210 may allow a user to download new routines for his or her robot from the cloud. For example, a laundry folding routine may be stored on the cloud, and a user may be able to select this routine using a mobile phone to download the routine from the cloud, and when the mobile phone is placed into or coupled to the robot, the robot would be able to perform the downloaded action.

In some examples, the client device 200 may be coupled to a mobile or cellular telephone to provide additional sensing capabilities. The cellular phone may not be physically attached to the robot, but may be coupled to the robot wirelessly. For example, a low cost robot may omit a direct connection to the Internet. This robot may be able to connect to a user's cellular phone via a wireless technology (e.g., Bluetooth) to be able to access the internet. The robot may be able to access various sensors and communication means of the cellular phone. The robot may not need as many sensors to be physically provided on the robot, however, the robot may be able to keep the same or similar functionality.

Thus, the client device 200 may include mechanical robot features, and may be configured to receive the device 210 (e.g., a mobile phone), which can provide additional peripheral components to the device 200, such as any of an accelerometer, gyroscope, compass, GPS, camera, WiFi connection, a touch screen, that are included within the device 210.

Figure 2B:
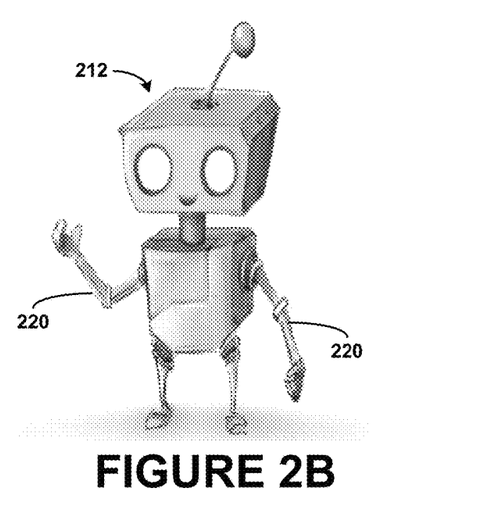
FIG. 2B illustrates a graphical example of a robot.

FIG. 2B illustrates a graphical example of a robot 212. In FIG. 2B, the robot 212 is shown as a mechanical form of a humanoid including arms, legs, and a head. The robot 212 may be configured to receive any number of modules or components, such a mobile phone, which may be configured to operate the robot. In this example, a device (e.g., robot 212) can be attached to a mobile phone (e.g., device 210) to provide the mechanical robot 212 with functionality enabling the robot 212 to communicate with the cloud to cause operation/functions of the robot 212. Other types of devices that have connectivity to the Internet can be coupled to robot 212 to provide additional functions on the robot 212. Thus, the device 210 may be separate from the robot 212 and can be attached or coupled to the robot 212.

In one example, the robot 212 may be a toy with only limited mechanical functionality, and by connecting device 210 to the robot 212, the toy robot 212 may now be capable of performing a number of functions with the aid of the device 210 and/or the cloud. In this manner, the robot 212 (or components of a robot) can be attached to a mobile phone to transform the mobile phone into a robot (e.g., with legs/arms) that is connected to a server to cause operation/functions of the robot.

The mountable device 210 may further be configured to maximize runtime usage of the robot 212 (e.g., if the robot 212 could learn what happens to cause the user to turn the toy off or set the toy down, the device 210 may be configured to perform functions to counteract such occurrences).

Figure 2C:
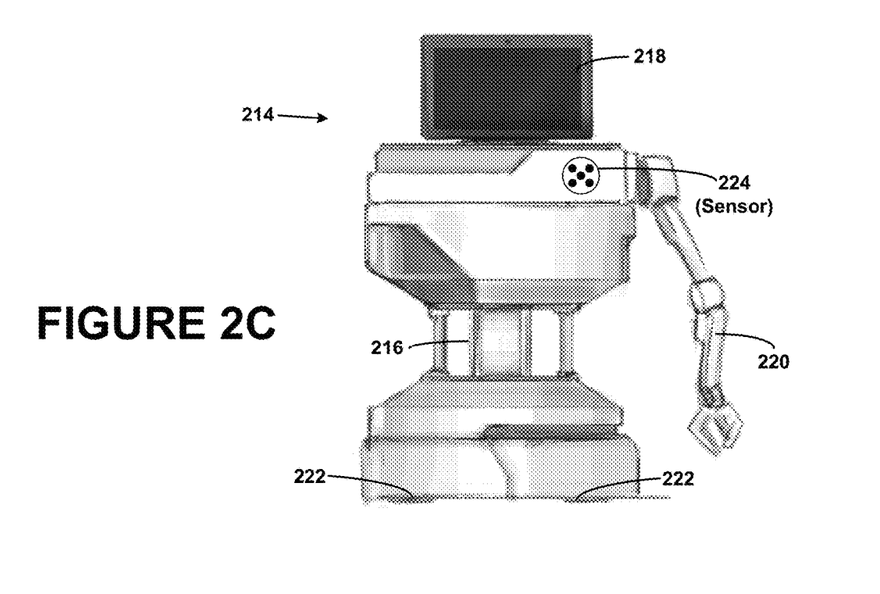
FIG. 2C illustrates another example of a robot.

FIG. 2C illustrates another example of a robot 214. The robot 214 includes a computing device 216, and a mechanical actuator 220. In this example, the computing device 216 may be a laptop computer or the equivalent thereof. Here, the robot has been provided with a video display or monitor 218, which may be coupled to sensors 224. The video monitor 218 could, as here, be used to project an image relating to a personality then being adopted by the robot 214. The sensors 224 may include a camera, infrared projectors, and other motion sensing or vision sensing elements. The robot 214 may include a base, wheels 222, and a motor upon which the computing device 216 and the sensors 218 can be positioned, for example.

Any of the robots illustrated in FIGS. 2A-2C may be configured to operate according to a robot operating system (e.g., an operating system designed for specific functions of the robot). A robot operating system may provide libraries and tools (e.g., hardware abstraction, device drivers, visualizers, message-passing, package management), to enable robot applications. Examples of robot operating systems include open source software such as ROS (robot operating system), DROS, or ARCOS (advanced robotics control operating system); proprietary software such as the robotic development platform ESRP from Evolution Robotics® and MRDS (Microsoft® Robotics Developer Studio), and other examples also include ROSJAVA. A robot operating system may include publish and subscribe functionality, and may also include functionality to control components of the robot, such as head tracking, base movement (e.g., velocity control, navigation framework).

3. Robot and Cloud Interaction

Figure 3:
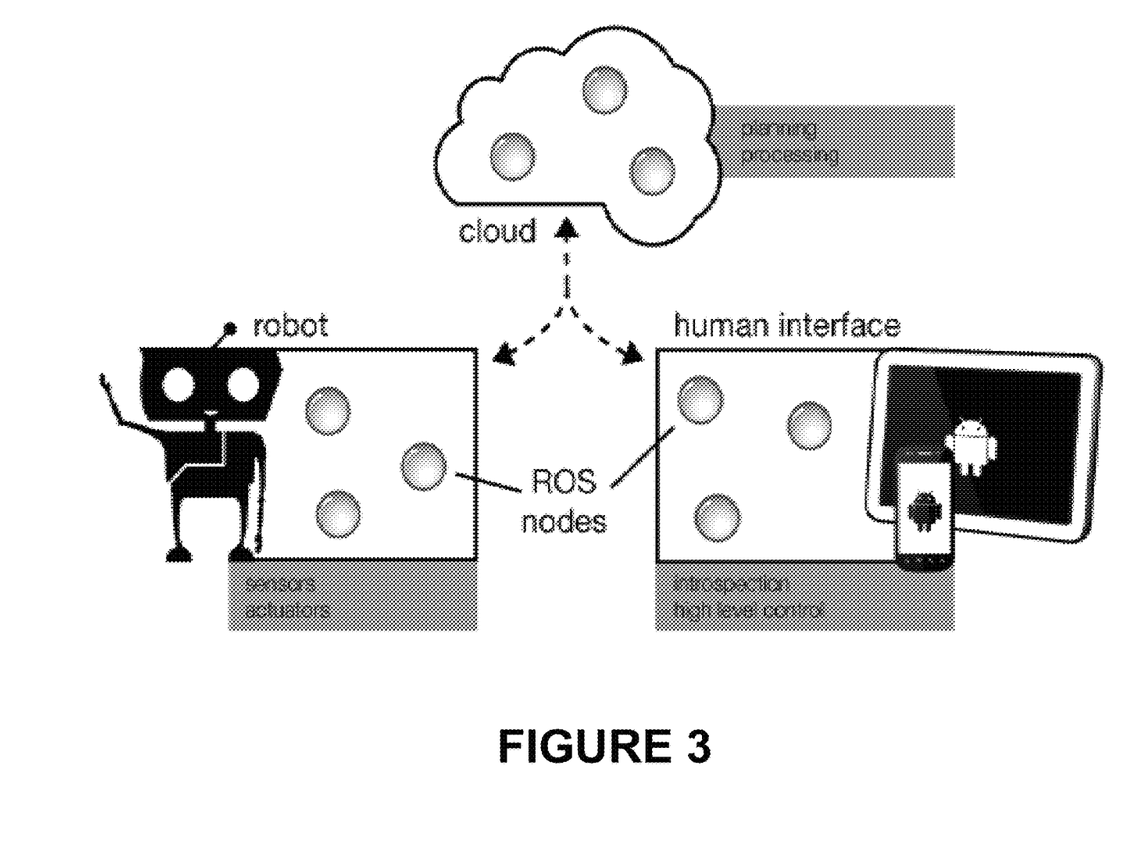
FIG. 3 illustrates an example of a conceptual robot-cloud interaction.

FIG. 3 illustrates an example of a robot-cloud interaction. A robot, such as a robot described and illustrated in FIG. 2A-C, may connect to a network of computers (e.g., the cloud), and may request data or processing to be performed by the cloud. In one example, the robot may include a number of sensors and mechanical actuators that may generally provide motor control for the robot. The sensor inputs to the robot, such as camera feeds, vision sensors, touch sensors and other clothing probes, may be provided to the cloud, which can process these outputs to the cloud to enable the robot to extract information and perform functions. The cloud may process a camera feed, for example, to determine a location of a robot, perform object recognition, as for something present in the vicinity or environment of the robot, or to indicate a navigation pathway for the robot.

FIG. 3 generally illustrates motor controllers in which each module may conceptually represent a computer or node on the cloud that performs processing using motor controller inputs or data from the robot. FIG. 3 also generally illustrates sensors in which each module may conceptually represent a computer or node on the cloud that performs processing using sensor inputs or data from the robot. FIG. 3 further generally illustrates applications in which each module may conceptually represent a computer or node on the cloud that performs specific functions of a number of applications, e.g., navigation application, mapping application. In addition, FIG. 3 further generally illustrates planning in which each module may conceptually represent a computer or node on the cloud that performs processing for the robot, such as general planning or computing processing.

As shown, any of the modules may be interconnected, and/or may communicate to receive data or instructions from each other so as to provide a specific output or functionality for the robot.

In one example, the robot may send sensory data of clothing attributes to a cloud for data processing, and in another example the robot may receive data back from the cloud based upon processing of that sensory data. The data received from the cloud may be in many different forms. The received data may be a processed form of data the robot sent to the cloud. The received data may also come from sources other than the robot. For example, the cloud may have access to other sensors, other robots, and the Internet.

Figure 4:
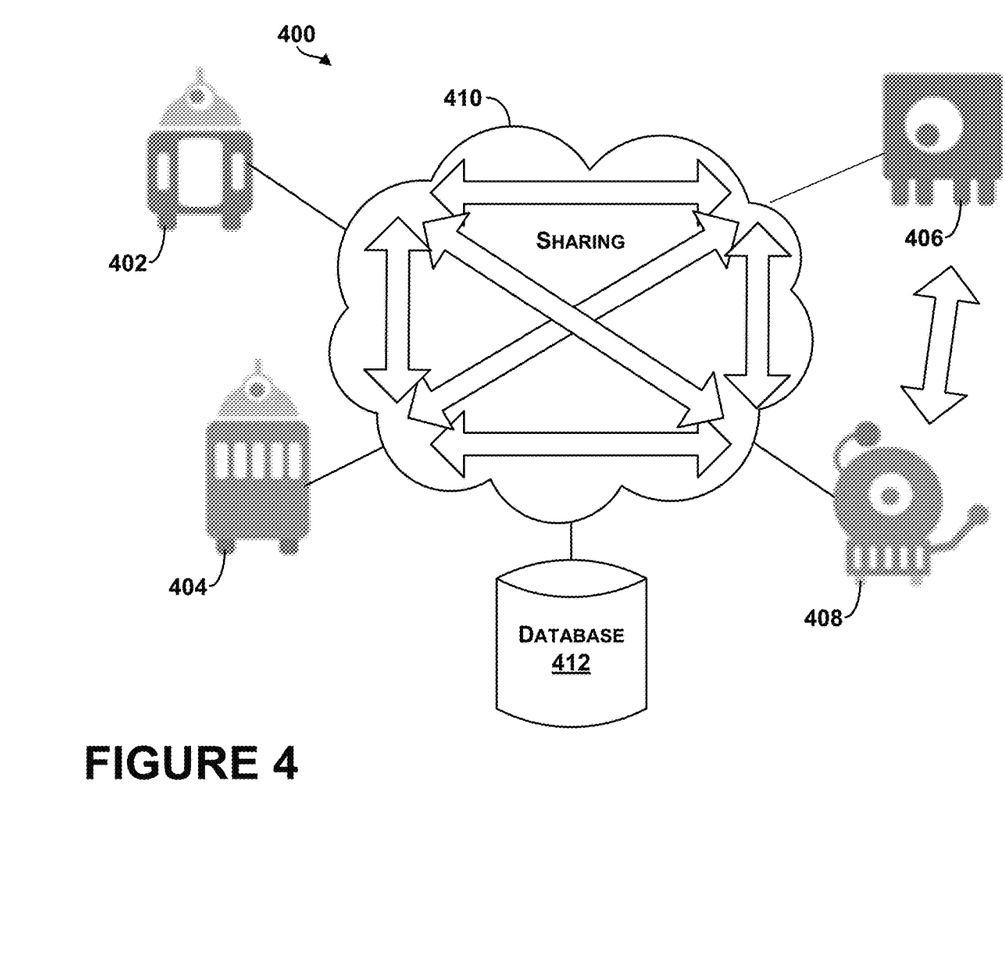
FIG. 4 is an example system in which robots may interact with the cloud and share information with other cloud computing devices.

FIG. 4 is an example system 400 in which robots may interact with the cloud and share information with other cloud computing devices. The system 400 illustrates robots 402, 404, 406, and 408 (e.g., as conceptual graphical representations) each coupled to a cloud 410. Each robot 402, 404, 406, and 408 may interact with the cloud 410, and may further interact with each other through the cloud 410, or through other access points and possibly directly (e.g., as shown between robots 406 and 408).

The cloud 410 may receive input from several robots. Data from each robot may be compiled into a larger data set. For example, the robot 402 may take a picture of an object (image) and upload the image to the cloud 410. An object recognition program in the cloud 410 may be configured to identify the object in the image and provide data to all the robots connected to the cloud 410 about the recognized object, as well as possibly about other characteristics (e.g., metadata) of the recognized object, such as a location, size, weight, color. Thus, every robot may be able to know attributes of an object in an image uploaded by the robot 402.

The robots 402, 404, 406 and 408 may perform any number of actions with an area, people, other robots. In one example, each robot 402, 404, 406 and 408 has WiFi or other network based connectivity and will upload/publish data to the cloud 410 that can then be shared with any other robot. In this manner, each robot 402, 404, 406 and 408 shares experiences with each other to enable learned behaviors. For example, the robot 402 may be in a showroom setting, evaluating a customer's selection of a clothing item. Robot 402 makes an assessment or determination based upon the observed clothing and/or user, which is then shared with the other robots 404, 406, and 408 (through the cloud 410). Each robot 402, 404, 406, and 408 will have access to real-time up to date data. One or more of these other robots may then proceed to perform some further function, such as obtaining a clothing selection in the correct size from a storeroom and delivering it to the customer. In another example, the robot 404 can download data indicating images seen by the other robots 402, 406, and 408 to help the robot 404 better identify an object using various views (e.g., in instances in which the robots 402, 406, and 408 have captured images of the object from a different perspective).

In still another example, the robot 408 may build a map of an area, and the robot 402 can download the map to have knowledge of the area. Similarly, the robot 402 could update the map created by the robot 408 with new information about the area (e.g., the hallway now has boxes or other obstacles), or with new information collected from sensors that the robot 408 may not have had (e.g., the robot 402 may be an outdoor robot, and may record and add temperature data to the map if the robot 408 did not have a temperature sensor). Overall, the robots 402, 404, 406, and 408 may be configured to share data that is collected to enable faster adaptation, such that each robot 402, 404, 406, and 408 can build upon a learned experience of a previous robot.

Sharing and adaptation capabilities enable a variety of applications based on a variety of inputs/data received from the robots 402, 404, 406, and 408.

In one example, the cloud 410 may include, store, or provide access to a database 412 of information related to objects, and the database 412 may be accessible by all the robots 402, 404, 406, and 408. The database 412 may include information identifying an object image or something in the image, and details of the object (e.g., mass, properties, shape, instructions for cleaning, cost, any detail that may be associated with the object) that can be accessed by the robots 402, 404, 406, and 408 to perform object recognition.

The database 412 may be accessible by all robots through the cloud 410 (or alternatively directly accessible by all robots without communication through the cloud 410). The database 412 may thus be a shared knowledge-base stored in the cloud 410.

Thus, in some examples, robots may share new or learned behaviors through the cloud 410. The cloud 410 may have a server that stores robot learned activities or behaviors resulting in a shared knowledge-base of behaviors and heuristics for object interactions (e.g., a robot "app store"). Specifically, a given robot may perform actions and build a compendium related to an article of clothing, and then the robot can upload the data to the cloud 410 to share this knowledge with all other robots. In this example, a transportation of the given robot's "consciousness" can be made through the cloud 410 from one robot to another (e.g., robot "Bob" builds up a "map" of some clothing, and the knowledge of "Bob" can be downloaded onto another robot to receive knowledge of the "map").

Thus, within examples, the robots 402, 404, 406, and 408 may share information through the cloud 410, and may access the database 412.

4. Robot-User Interactions

As mentioned, robots (or any client computing device) may interact with the cloud and users to perform any number of functions. Example functions are described below.

Figure 5:
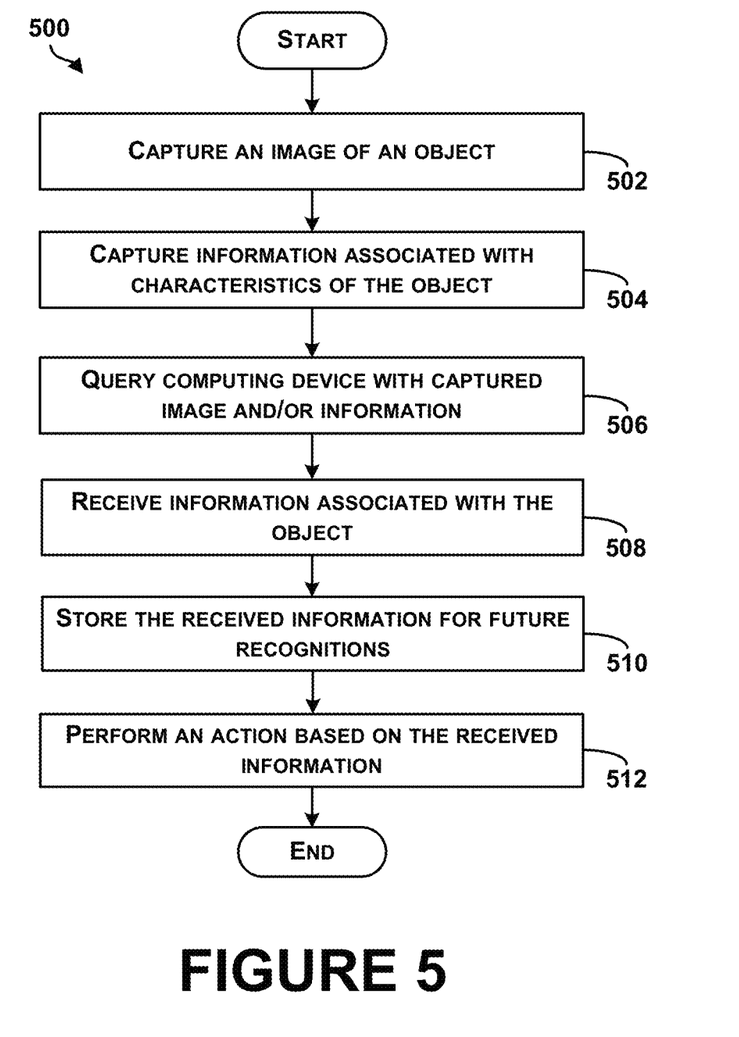
FIG. 5 is a block diagram of an example method of a robot interaction with the cloud to facilitate object recognition.

FIG. 5 is a block diagram of an example method of a robot interaction with the cloud to facilitate object recognition, in accordance with at least some embodiments described herein. Method 500 shown in FIG. 5 presents an embodiment of a method that, for example, could be used with the systems 100 and 400, for example, and may be performed by a device, such as another devices illustrated in FIGS. 1-4, or components of the device. Method 500 may include one or more operations, functions, or actions as illustrated by one or more of blocks 502-512. Although the blocks are illustrated in a sequential order, these blocks may also be performed in parallel, and/or in a different order than those described herein, unless dictated by a necessary earlier step. Also, the various blocks may be combined into fewer blocks, divided into additional blocks, and/or removed based upon the desired implementation.

In addition, for the method 500 and other processes and methods disclosed herein, the flowchart shows functionality and operation of one possible implementation of present embodiments. In this regard, each block may represent a module, a segment, or a portion of program code, which includes one or more instructions executable by a processor for implementing specific logical functions or steps in the process. The program code may be stored on any type of computer readable medium, for example, such as a storage device including a disk or hard drive. The computer readable medium may include non-transitory computer readable medium, for example, such as computer-readable media that stores data for short periods of time like register memory, processor cache and Random Access Memory (RAM). The computer readable medium may also include non-transitory media, such as secondary or persistent long term storage, like read only memory (ROM), optical or magnetic disks, compact-disc read only memory (CD-ROM), for example. The computer readable media may also be any other volatile or non-volatile storage systems. The computer readable medium may be considered a computer readable storage medium, for example, or a tangible storage device.

In addition, for the method 500 and other processes and methods disclosed herein, each block in FIG. 5 may represent circuitry that is wired to perform the specific logical functions in the process.

At block 502, the method 500 includes capture an image of an object. In an example, a robot may capture many images of objects using any number of sensors, such as a camera (still pictures or video feeds), infrared projectors, and other sensors as discussed herein.

At block 504, the method 500 includes capture information associated with characteristics about the object. For example, a robot may optionally determine or record dimensions, a texture, color, pattern, material, shape or any type of physical attribute of the object.

As another example, in an instance in which the robot may communicate with the object, the robot may capture additional data of the object, such as by accessing a magnetic strip, RFID, near field communication clip, bar code, of the clothing item. The robot may thereby communicate with the clothing to determine many types of data.

At block 506, the method 500 includes query a computing device with the captured image and/or information. As an example, the robot may query the cloud with a captured image by sending the captured image to the cloud and requesting information about the image, such as an identity of the image or information associated with characteristics of the clothing in the image. Alternatively, the robot may query another robot directly to provide or request information about the object. This may be a command robot, as described herein.

At block 508, the method 500 includes receiving information or retrieving information associated with the object. For example, the robot may receive data from the cloud, as by processing and a command function from the command robot, indicating an identity of the object in the image, or other information related to or associated with characteristics about the object, with directions from the command robot to proceed according to a task involving the object.

At block 510, the method 500 includes storing the received information for future use. For example, after receiving the information from the cloud, the robot would be able to recognize the object in the future enabling the robot to learn and adapt. Storing is an optional step.

At block 512, the method 500 includes performing an action based on the received information from the command robot. The action may vary based on a type of received information.

5. Robot-Robot Interactions

Figure 6:
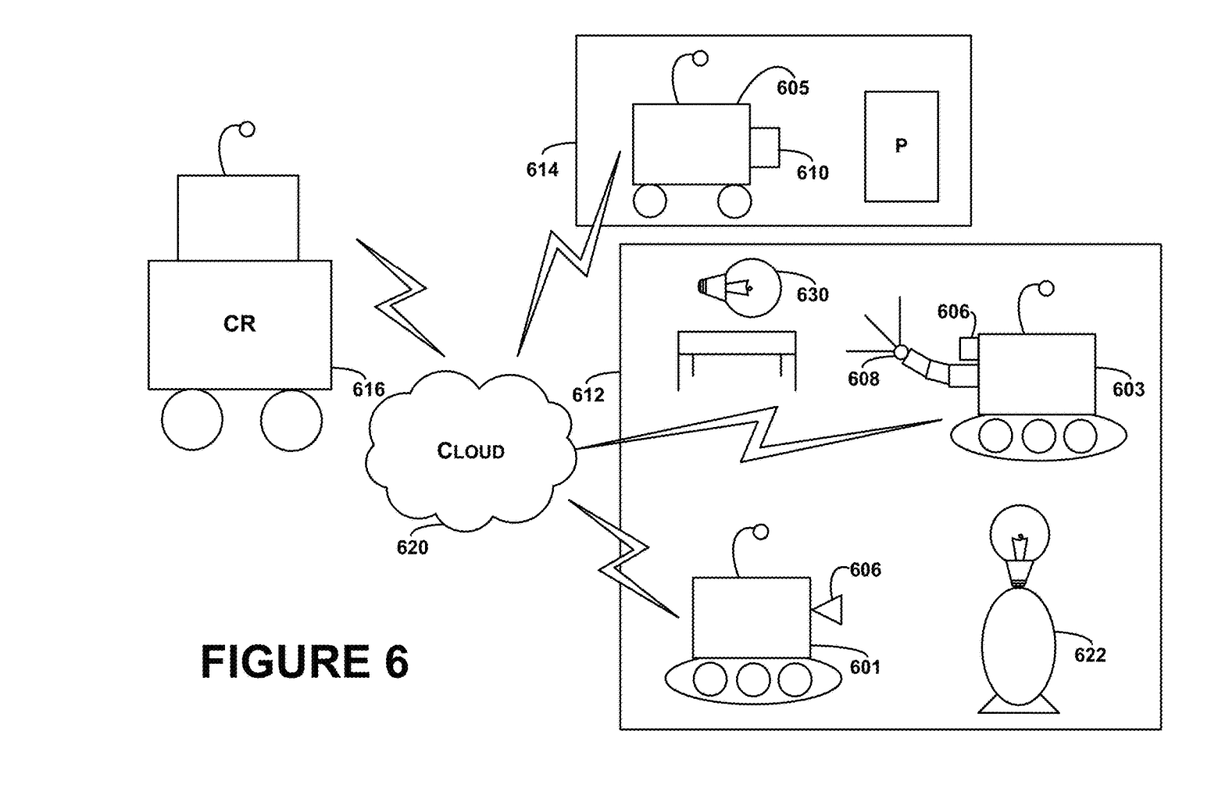
FIG. 6 is an example system in which robots may interact with the cloud and share information with each other, a command robot, and other cloud computing devices, all arranged in accordance with at least some embodiments described herein.

FIG. 6 is an exemplary illustration of a method and system having a multiplicity of client or follower robots 601, 603 and 605 (robotic apparatus) interacting with various aspects of their environment, to perform functions as described in FIG. 5, for instance. The client robots can have standard attributes of a computing system, including a CPU, memory and an operating system. In this example, the client robots have some differing attributes or capabilities. For instance, robot 601 has a visual sensor in the form of a camera 606. Robot 603 has an appendage 608 that can manipulate things in its environment. Robot 605 has an electronic data sensor 610 for electronic data capture. In other examples, the robots may all have the same capabilities and functionalities, but may be in differing locations or circumstances, thus obtaining different data. In the example shown in FIG. 6, robots 601 and 603 occupy the same general vicinity in a room 612, whereas robot 605 is located in a different room, room 614. Room 614 includes a power source P.

The system shown in FIG. 6 has a command or leader robot (CR) 616. Command robot 616 can the same general components as the client robots, but also includes a command program for interacting with the client robots. The command program can include functionality and executable instructions for communicating with the client robots, and performing command functions directing the conduct or action of one or more, or all, of the client robots.

The communication between the command robot 616 and the client robots can occur through a cloud computing system 620, as described above. In the scenario depicted in FIG. 6, client robot 601 obtains sensory data using the camera 606 that the light fixture 622 is not functioning (is not lighting). This sensory data is transmitted through the cloud 620 to the command robot 616. Command robot 616 processes that data input from client robot 601, and determines that client robot 605 is in an area where the power source P for the light fixture 622 can be accessed. Command robot 616 then performs an output function to direct client robot 605 to do an electronic data capture to determine if power is flowing to the light fixture 622. Client robot 605 makes the data capture that the power is operating, and that input is relayed through the cloud 620 to the command robot 616. Command robot 616 ascertains that client robot 603 is present in the room 612, and performs a further output function by directing client robot 603 to retrieve a new light bulb 630 to replace that in the light fixture 622.

Client robot 601 is then accessed again by the command robot 616 to obtain sensory image data regarding whether the new light bulb 630 is operating in the light fixture 622, and the image data processed indicate that the light bulb 630 is glowing. That further data capture is then relayed to command robot 616, which based upon this feedback from client robot 601, now directs client robot 603 to dispose of the non-functioning light bulb.

In some examples, the methodology of application to facilitate object recognition may be a higher-level service (e.g., higher in a software stack), such that details and specifics for how to recognize an object may be performed by the cloud. The robot may be configured to perform actions/functions based on a result of object recognition, rather than or in addition to, performing functions regarding recognizing an object. As an example, using the application, the robot 603 may execute software to perform immediate function calls, such as OrientObject( ) which may return information associated with an object (e.g., placing it right-side up), or RotateObject( ) which may cause the robot 603 to pick up the object and obtain further views/sensory inputs. These immediate functions could be done through local processing within the robot 603, or by enabling function calls and operation through the cloud 620, which greatly facilitates control and operation of the robot without having to control or tie-up more limited computational capacities of the robot, for example.

CONCLUSION

It should be understood that arrangements described herein are for purposes of example only. As such, those skilled in the art will appreciate that other arrangements and other elements (e.g., machines, interfaces, functions, orders, and groupings of functions) can be used instead, and some elements may be omitted altogether according to the desired results. Further, many of the elements that are described are functional entities that may be implemented as discrete or distributed components or in conjunction with other components, in any suitable combination and location.

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims, along with the full scope of equivalents to which such claims are entitled. It is also to be understood that the terminology used herein is for the purpose of describing particular embodiments only, and is not intended to be limiting.

What is claimed is:

1. A method comprising:
   receiving, by a command robot, sensory data captured by a first client robot, wherein the command robot is in communication with the first client robot and a second client robot, wherein the first client robot has a first sensing capability and the second client robot has a second sensing capability that is different than the first sensing capability, wherein the sensory data is captured by way of the first sensing capability of the first client robot, wherein the first client robot has a first functionality and the second client robot has a second functionality that is different than the first functionality, wherein the sensory data is relevant to the second functionality of the second client robot;
   providing, by the command robot, at least a portion of the sensory data captured by the first client robot as a first input to the second client robot, wherein the portion of the sensory data is relevant to the second functionality of the second client robot;
   receiving feedback from the second client robot based on the first input; and
   commanding, by the command robot, the second client robot to perform a task by way of the second functionality based on the feedback and the portion of the sensory data captured by the first client robot.

2. The method of claim 1, further comprising:
   receiving further sensory data from the first client robot; and
   commanding the first client robot to perform an additional task based on the further sensory data.

3. The method of claim 1, wherein each of the first client robot and the second client robot include at least one sensor comprising one or more of an image capture device, an acoustic sensor device, and an electronic data acquisition device.

4. The method of claim 1, wherein the first sensing capability is related to capturing environment sensory data associated with a condition of an environment of the first client robot, and wherein the second sensing capability is related to sensing state of a device configured to adjust the condition of the environment of the first client robot.

5. The method of claim 1, wherein the command robot is in communication with the first client robot and the second client robot by way of a cloud computing system, wherein the cloud computing system includes at least one server remote from the command robot, the first client robot, and the second client robot, and wherein the at least one server is configured to store at least a portion of the sensory data and facilitate communication between the command robot and the first and second client robots.

6. The method of claim 1, wherein at least one of the first client robot and the second client robot comprises one or more mechanical actuators and configured to receive a removable module that includes wireless communication capability, wherein the command robot is configured to communicate with the at least one of the first client robot and the second client robot by way of the wireless communication capability.

7. A non-transitory computer readable memory having stored thereon instructions that, when executed by a command robot, cause the command robot to perform operations comprising:
- receiving sensory data captured by a first client robot, wherein the command robot is in communication with the first client robot and a second client robot, wherein the first client robot has a first sensing capability and the second client robot has a second sensing capability that is different than the first sensing capability, wherein the sensory data is captured by way of the first sensing capability of the first client robot, wherein the first client robot has a first functionality and the second client robot has a second functionality that is different than the first functionality, wherein the sensory data is relevant to the second functionality of the second client robot;
- providing at least a portion of the sensory data captured by the first client robot as a first input to the second client robot, wherein the portion of the sensory data is relevant to the second functionality of the second client robot;
- receiving feedback from the second client robot based on the first input; and
- commanding the second client robot to perform a task by way of the second functionality based on the feedback and the portion of the sensory data captured by the first client robot.

8. The non-transitory computer readable memory of claim 7, wherein the operations further comprise:
- receiving further sensory data from the first client robot; and
- commanding the first client robot to perform an additional task based on the further sensory data.

9. The non-transitory computer readable memory of claim 7, wherein each of the first client robot and the second client robot include at least one sensor comprising one or more of an image capture device, an acoustic sensor device, and an electronic data acquisition device.

10. The non-transitory computer readable memory of claim 7, wherein the first sensing capability is related to capturing environment sensory data associated with a condition of an environment of the first client robot, and wherein the second sensing capability of the second client robot is related to sensing state of a device configured to adjust the condition of the environment of the first client robot.

11. The non-transitory computer readable memory of claim 7, wherein the command robot is in communication with the first client robot and the second client robot by way of a cloud computing system, wherein the cloud computing system includes at least one server remote from the command robot, the first client robot, and the second client robot, and wherein the at least one server is configured to store at least a portion of the sensory data and facilitate communication between the command robot and the first and second client robots.

12. The non-transitory computer readable memory of claim 7, wherein at least one of the first client robot and the second client robot comprises one or more mechanical actuators and configured to receive a removable module that includes wireless communication capability, wherein the command robot is configured to communicate with the at least one of the first client robot and the second client robot by way of the wireless communication capability.

13. A system comprising:
- a first client robot having a first sensing capability and a first functionality;
- a second client robot having a second sensing capability that is different than the first sensing capability and a second functionality that is different than the first functionality; and
- a command robot in communication with the first client robot and the second client robot, wherein the command robot comprises at least one processor, a memory, and program instructions stored in the memory that when executed by the at least one processor cause the command robot to perform operations comprising:
  - receiving sensory data captured by the first client robot by way of the first sensing capability, wherein the sensory data is relevant to the second functionality of the second client robot;
  - providing at least a portion of the sensory data captured by the first client robot as a first input to the second client robot, wherein the portion of the sensory data is relevant to the second functionality of the second client robot;
  - receiving feedback from the second client robot based on the first input; and
  - commanding the second client robot to perform a task by way of the second functionality based on the feedback and the portion of the sensory data captured by the first client robot.

14. The system of claim 13, wherein the operations further comprise:
- receiving further sensory data from the first client robot; and
- commanding the first client robot to perform an additional task based on the further sensory data.

15. The system of claim 13, wherein each of the first client robot and the second client robot include at least one sensor comprising one or more of an image capture device, an acoustic sensor device, and an electronic data acquisition device.

16. The system of claim 13, wherein the first sensing capability is related to capturing environment sensory data associated with a condition of an environment of the first client robot, and wherein the second sensing capability of the second client robot is related to sensing state of a device configured to adjust the condition of the environment of the first client robot.

17. The system of claim 13, further comprising:
- a cloud computing system, wherein the command robot is in communication with the first client robot and the second client robot by way of the cloud computing system, wherein the cloud computing system includes at least one server remote from the command robot, the first client robot, and the second client robot, and wherein the at least one server is configured to store at least a portion of the sensory data and facilitate communication between the command robot and the first and second client robots.

* * * * *